United States Patent

Depui et al.

Patent Number: 6,132,771
Date of Patent: *Oct. 17, 2000

[54] ORAL PHARMACEUTICAL DOSAGE FORMS COMPRISING A PROTON PUMP INHIBITOR AND A PROKINETIC AGENT

[75] Inventors: Helene Depui, Göteborg; Agneta Hallgren, Mölndal, both of Sweden

[73] Assignee: AstraZeneca AB, Sodertalje, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,936
[22] PCT Filed: Dec. 20, 1996
[86] PCT No.: PCT/SE96/01736
   § 371 Date: Feb. 13, 1997
   § 102(e) Date: Feb. 13, 1997
[87] PCT Pub. No.: WO97/25065
   PCT Pub. Date: Jul. 17, 1997

[30] Foreign Application Priority Data

Jan. 8, 1996 [SE] Sweden ................................ 9600072

[51] Int. Cl.⁷ .............................. A61K 9/22; A61K 9/30; A61K 9/26; A61K 9/50
[52] U.S. Cl. .......................... 424/468; 424/469; 424/470; 424/475; 424/490; 424/482; 424/480; 424/460; 514/925
[58] Field of Search ..................... 424/468, 465, 424/467, 475, 469, 494, 480, 489, 490, 470, 474, 460, 482; 514/925

[56] References Cited

U.S. PATENT DOCUMENTS 4,786,505 11/1988 Lovgren et al. .................... 424/468
5,330,982 7/1994 Tyers .
5,753,265 5/1998 Bergstrand et al. .
5,817,338 10/1998 Bergstrand et al. .

FOREIGN PATENT DOCUMENTS 0008780 3/1980 European Pat. Off. .
0013566 7/1980 European Pat. Off. .
0072021 8/1982 European Pat. Off. .
0080341 6/1983 European Pat. Off. .
0108295 5/1984 European Pat. Off. .

(List continued on next page.)

OTHER PUBLICATIONS

Vigneri et al. 1995 "A comparison of five maintenance therapies . . ." The N.E.J. of Medicine 333: 1106–1110, Oct. 26, 1995.

Boer et al. 1994 "Review article: drug therapy for reflux oesophagitis" Aliment Pharmacol. Ther. 8: 147–157.

Inauen et al. 1993 "Effects of ranitidine and cisapride on acid reflux" Gut 34: 1025–1031.

*Primary Examiner*—Thurman K. Page
*Assistant Examiner*—Brian K Seidleck
*Attorney, Agent, or Firm*—White & Case LLP

[57] ABSTRACT

An oral pharmaceutical dosage form comprising a proton pump inhibitor and one or more prokinetic agents in a fixed formulation, wherein the proton pump inhibitor is protected by an enteric coating layer. The fixed formulation is in the form of multilayered tablets, capsules or multiple unit tableted dosage forms. The multiple unit dosage forms are most preferred. The new fixed formulation is especially useful in the treatment of disorders associated with gastro oesophageal reflux diseases.

22 Claims, 1 Drawing Sheet

FOREIGN PATENT DOCUMENTS

| | | |
|---|---|---|
| 0108504 | 5/1984 | European Pat. Off. . |
| 0111103 | 6/1984 | European Pat. Off. . |
| 0170752 | 2/1986 | European Pat. Off. . |
| 0247983 | 12/1987 | European Pat. Off. . |
| 0365947 | 5/1990 | European Pat. Off. . |
| 0391518 | 10/1990 | European Pat. Off. . |
| 0426479 | 5/1991 | European Pat. Off. . |
| 0541369 | 5/1993 | European Pat. Off. . |
| 0587220 | 3/1994 | European Pat. Off. . |
| 0648487 | 4/1995 | European Pat. Off. . |
| 2066070 | 7/1981 | United Kingdom . |
| 2091097 | 7/1982 | United Kingdom . |
| 2132887 | 7/1984 | United Kingdom . |
| 2285989 | 8/1995 | United Kingdom . |
| 8501207 | 3/1985 | WIPO . |
| 8503436 | 8/1985 | WIPO . |
| 8702240 | 4/1987 | WIPO . |
| 9312772 | 7/1993 | WIPO . |
| 9403160 | 2/1994 | WIPO . |
| 9501803 | 1/1995 | WIPO . |
| 9510264 | 4/1995 | WIPO . |
| 9725065 | 7/1997 | WIPO . |

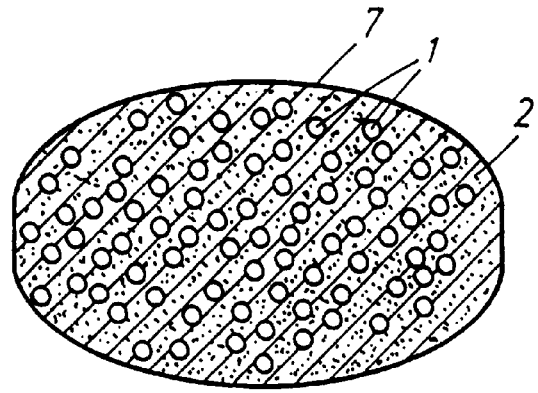
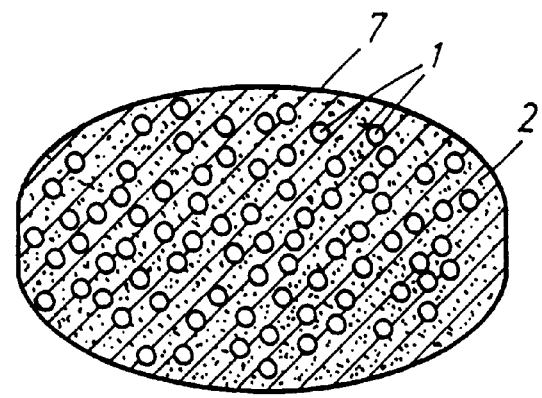
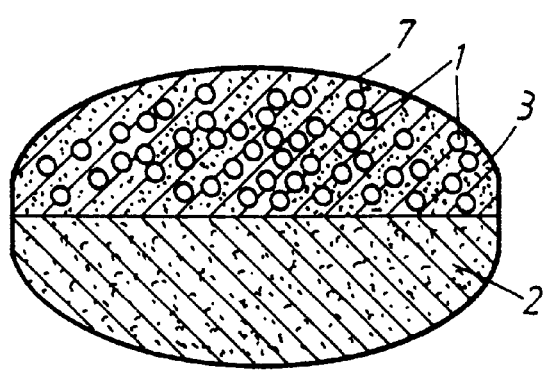
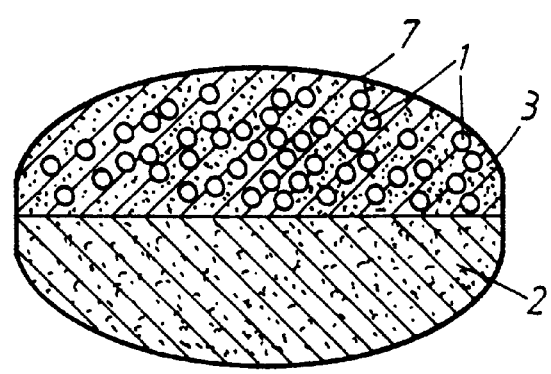
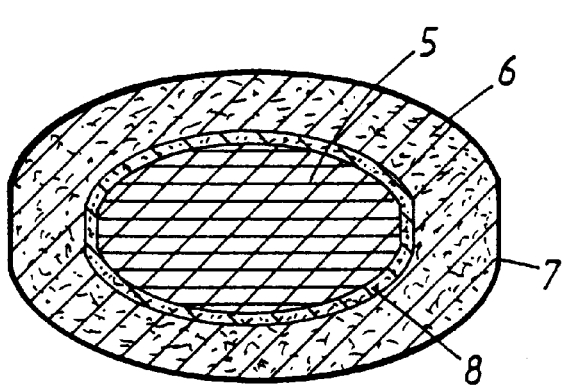
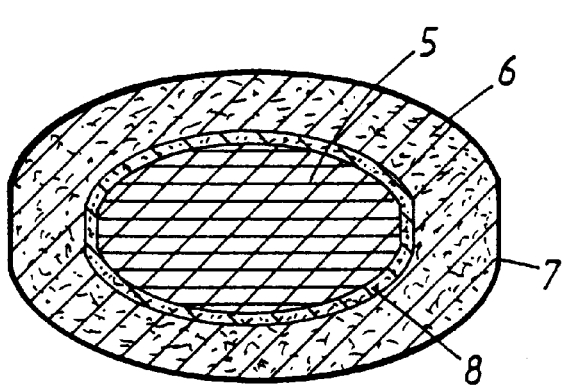
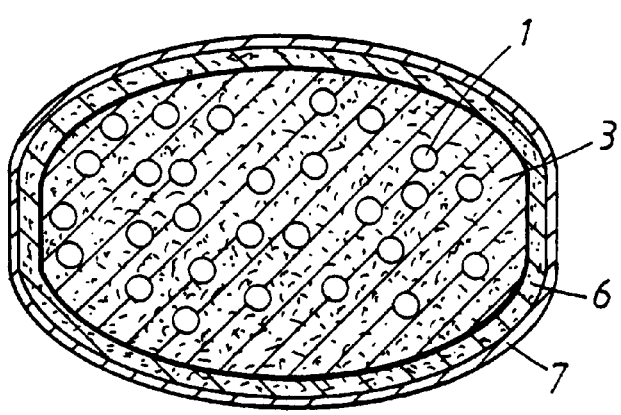
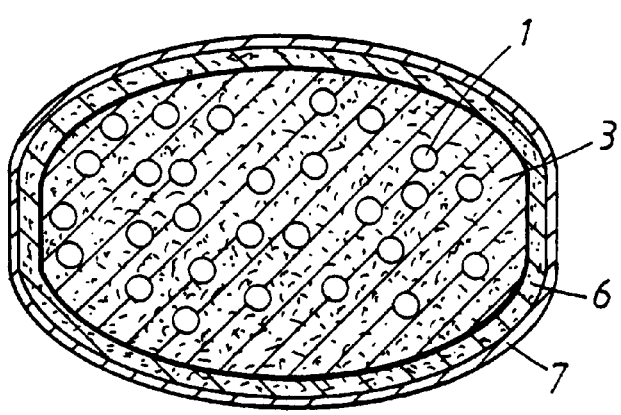

ORAL PHARMACEUTICAL DOSAGE FORMS COMPRISING A PROTON PUMP INHIBITOR AND A PROKINETIC AGENT

This application is a 371 of PCT/SE96/01736, filed Dec. 20, 1996.

FIELD OF THE INVENTION

The present invention is related to new oral pharmaceutical preparations especially for use in the prevention and treatment of disorders associated with gastro oesophageal reflux. The present preparations comprise a gastric acid suppressing agent, such as a proton pump inhibitor, in combination with one or more prokinetic agents in a new fixed unit dosage form, especially a tablet. Furthermore, the present invention refers to a method for the manufacture of such preparations and the use of such preparations in medicine, especially in the treatment of gastro oesophageal reflux diseases and other gastrointestinal disorders.

BACKGROUND OF THE INVENTION

Gastro oesophageal reflux disease (GORD) is among the most common disorders seen by gastroenterologists and general practicians. The wide diversity of symptoms and disease severity produced by acid reflux has led to the need for more individualized treatment strategies. Therapeutic agents effective in the treatment of GORD include gastric acid suppressing agents, such as $H_2$ receptor antagonists, proton pump inhibitors, other agents of interest are antacids/alginates and prokinetic agents. These agents can be distinguished by their mechanisms of action, safety profile, pharmacokinetics and indications.

Antacids and alginates are still widely used. They have a short duration of action but are seen as inexpensive and safe. They do not provide a layterm symptom resolution of GORD.

$H_2$ receptor antagonists are widely prescribed for GORD. Their higher cost has been compensated by the clinical results obtained both in terms of symptom relief and healing. These advantages have been related to their mode of action, which offered more potent and longer duration of effect on gastric acidity.

Proton pump inhibitors, such as omeprazole, are rapidly taking share from $H_2$ receptor antagonists, particularly in reflux oesophagitis. Omeprazole is known to offer significant gain over $H_2$ receptor antagonists in terms of symptom resolution, healing and prevention of relapse for reflux oesophagitis.

Prokinetic agents of the first generation, e.g. bethanecol, stimulates cholinergic receptors, and of the second generation, e.g. domperidone and metoclopramide, blocks effects of endogenous dopamine in the gut. The results of double-blind placebo controlled trials in GORD patients have been conflicting. The action of the third generation of prokinetic agents, such as substituted benzamides, e.g. cisapride and mosapride derives primarily, but not exclusively, from facilitating acetylcholine release from neurones of the myenteric plexus via stimulation of 5-HT4 receptors. The efficacy of orally administered benzamides, such as cisapride, in patients with GORD and reflux oesophagitis has been studied and a superior effect in alleviating gastro-oesophageal symptoms and healing low grade oesophagitis (non circumferential erosion) has been shown in most studies.

Patients with severe symptoms, severe mucosal damage or both are almost always treated with proton pump inhibitors for profound and long-term control of gastric acid secretion. Patients with mild symptoms and limited mucosal damage respond best to H2-receptor antagonist, prokinetic agents or proton pump inhibitors.

A combination therapy of a prokinetic agent and a gastric acid lowering compound is rational and was shown more effective than mono therapy apart from full dose of proton pump inhibitors. Administration of cisapride and ranitidine was shown to further lower the exposure of the oesophagus to acid(s) (Inauen W et al. Gut 1993; 34: 1025–1031). Such a therapy was also shown to improve healing rates (de Boer WA et al. Aliment Pharmacol Ther 1994; 8: 147–157). WO 95/01803 describes a pharmaceutical composition of famitidine, cisapride and optionally simethicone in the treatment of gastrointestinal distress.

Maintenance therapy is often necessary to prevent recurrent symptoms and oesophagitis. Recently a combination therapy combining an acid-suppressing medication with a prokinetic (cisapride) was shown also very effective. Further, Vyneri et al (N. Engl. J Med 1995; 333: 1106–1110) found that omeprazole alone or in combination with cisapride was more effective than ranitidine alone or cisapride alone and that omeprazole combined with cisapride was more effective than ranitidine plus cisapride. Such combination therapies might be considered for patients whose predominant symptom is regurgitation; those whose symptoms occur mainly at night; those with respiratory problems such as posterior laryngitis, asthma, chronic bronchitis, or recurrent aspiration; those with cough and hoarseness related to reflux disease.

A combination therapy comprising an acid suppressing agent and a prokinetic agent is attractive, rational and effective. An acid suppressing agent plus a prokinetic agent could be an alternative to each of them separately in case of failure. However, because of the large number of therapeutical tablets/pills that must be taken each day in such a therapy, the compliance of such a treatment may be a problem. It is well known that patient compliance is a main factor in receiving good results in medical treatments. Administration of two, three or even more different tablets to the patient is not convenient or satisfactory to achieve the most optimal results. The present invention now provides new oral dosage forms comprising two or more different active substances combined in one fixed unit dosage form, preferably a tablet.

It is well known that some of the gastric acid suppressing agents, such as proton pump inhibitors are susceptible to degradation/transformation in acid reacting and neutral media. In respect of the stability properties, it is obvious that the one of the active substances being an acid susceptible proton pump inhibitor must be protected from contact with acidic gastric juice by an enteric coating layer. There are different enteric coating layered preparations of proton pump inhibitors described in the prior art, see for example U.S. Pat No. 4,786,505 (AB Hässle) describing a preparation comprising omeprazole.

There are problems to produce a fixed unit dosage form comprising a rather high amount of active substance. Different active substances with differing physical properties in the same preparation give further problems. Preparation of a multiple unit tableted dosage form encounters specific problems when enteric coating layered pellets containing acid susceptible proton pump inhibitors as active substance are compressed into tablets. If the enteric coating layer does not withstand the compression of the pellets into a tablet the susceptible active substance will be destroyed by penetrating acidic gastric juice, i.e. the acid resistance of the enteric coating layer of the pellets will not be sufficient in the tablet after compression.

SUMMARY OF THE INVENTION

The present invention provides oral, fixed unit dosage forms, i.e. a multiple unit tableted dosage forms, multilayered tablets or a capsule filled with more than one pharmaceutically active compound. The active compounds present in the dosage form are preferably an acid susceptible proton pump inhibitor which is protected by an enteric coating layer, and one or more prokinetic agents. These new dosage forms will simplify the regimen and improve the patient compliance.

BRIEF DESCRIPTION OF THE DRAWINGS

FIG. 1 illustrates a cross-section of a multiple unit tableted dosage form comprising an acid susceptible proton pump inhibitor in the form of enteric coating layered pellets (1) in admixture with a prokinetic agent and pharmaceutically acceptable excipients (2). The tablet is covered by a filmcoating layer, i.e. tablet coat (7).

FIG. 2 illustrates a cross-section of a tablet with two separate layers, one of which comprising enteric coating layered pellets (1) in admixture with excipients (3) and the other layer comprising the prokinetic agent in admixture with pharmaceutically acceptable excipients (2). The tablet is covered by a filmcoating layer (7).

FIG. 3 illustrates a cross-section of an enteric coating layered tablet comprising a proton pump inhibitor in admixture with pharmaceutically acceptable excipients in the tablet core (5) surrounded by an enteric coating layer (8) and thereupon a layer of the prokinetic agent(s) in admixture with pharmaceutically acceptable excipients (6). The tablet is covered by a filmcoating layer (7).

FIG. 4 illustrates a cross-section of a multiple unit tableted dosage form comprising an acid susceptible proton pump inhibitor in the form of enteric coating layered pellets (1) in admixture with excipients (3) and on the multiple unit tableted dosage form a layer comprising the prokinetic agent(s) in admixture with pharmaceutically acceptable excipients (6). The tablet is covered by a filmcoating layer (7).

DETAILED DESCRIPTION OF THE INVENTION

One object of the invention is to provide an oral, multiple unit tableted dosage form comprising an acid susceptible proton pump inhibitor in the form of individually enteric coating layered units together with one or more prokinetic agents in the form of a powder or granules compressed into a tablet. The enteric coating layer(s) covering the individual units of the proton pump inhibitor has properties such that the compression of the units into a tablet does not significantly affect the acid resistance of the individually enteric coating layered units. Furthermore, the multiple unit tableted dosage form provides a good stability of the active substances during long-term storage.

The new fixed dosage form is preferably in the form of a multiple unit tableted dosage form comprising enteric coating layered units of the one of the active substance which is acid susceptible and granules of the other active substance, i.e. prepared prokinetic granules as shown in FIG. 1.

The proton pump inhibitor, in the form of enteric coating layered units, may also be mixed with pharmaceutically acceptable excipients and compressed into a tablet which is then filmcoated with an aqueous suspension containing the prokinetic substance, see FIG. 4.

Another object of the invention is to provide a tablet preparation comprising a proton pump inhibitor in admixture with tablet excipients in a tablet core and a separate layer surrounding the tablet core, which layer comprises one or more prokinetic agent(s) presscoated onto the tablet core. The tablet core is enteric coating layered before the surrounding layer of prokinetic agents is applied. Optionally a separating layer also is applied on the tablet before the enteric coating layer, see FIG. 3.

Alternatively, the prepared tablet is sectioned in separate layers, each one comprising different active substances. Preferably one layer comprises the proton pump inhibitor in the form of enteric coating layered pellets in admixture with pharmaceutically acceptable excipients and another layer(s) comprises(-e) the prokinetic agent(s) in admixture with pharmaceutically acceptable excipients, respectively, see FIG. 2.

A further object of the invention is to provide a multiple unit tableted dosage form, which is divisible and easy to handle. Such a multiple unit tableted dosage form may be dispersed in an aqueous liquid and can be given to patients with swallowing disorders and in pediatrics. Such a suspension of dispersed units/pellets of appropriate size can be used for oral administration and also for feeding through a naso-gastric tube.

Furthermore, the present invention provides a capsule preparation comprising the proton pump inhibitor in the form of enteric coating layered pellets mixed with one or more prokinetic agents in the form of prepared granules or pellets. The new fixed unit dosage forms comprise as active substances one gastric acid suppressing agent, such as an acid susceptible proton pump inhibitor and one or more prokinetic agents. The different therapeutically active components used in the dosage forms are defined below.

The prokinetic part of the formulation may be formulated in the form of instant release, sustained release or extended release formulations. Alternatively, all the components of the formulation may be formulated in an effervescent formulation.

ACTIVE SUBSTANCES

The gastric acid suppressing agent is preferably an acid susceptible proton pump inhibitor. Such proton pump inhibitors are for example compounds of the general formula I

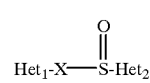

wherein $Het_1$ is

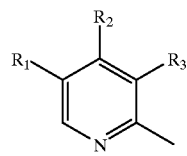 or 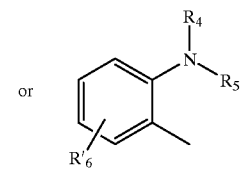

-continued

Het₂ is

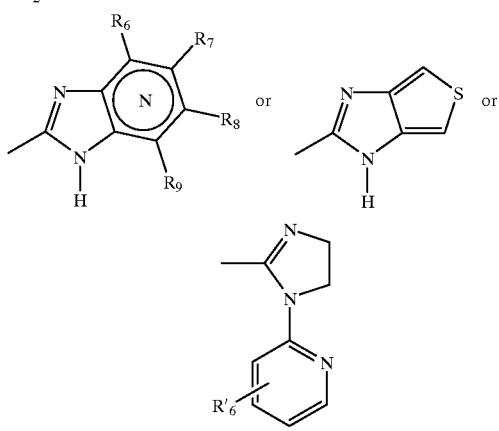

X =

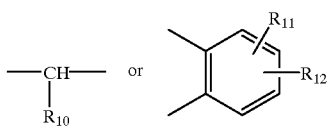

wherein

- N in the benzimidazole moiety means that one of the carbon atoms substituted by $R_6$–$R_9$ optionally may be exchanged for a nitrogen atom without any substituents;
- $R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;
- $R_4$ and $R_5$ are the same or different and selected from hydrogen, alkyl and aralkyl; $R_6'$ is hydrogen, halogen, trifluoromethyl, alkyl and alkoxy; $R_6$–$R_9$ are the same or different and selected from hydrogen, alkyl, alkoxy, halogen, haloalkoxy, alkylcarbonyl, alkoxycarbonyl, oxazolyl, trifluoroalkyl, or adjacent groups $R_6$–$R_9$ form ring structures which may be further substituted;
- $R_{10}$ is hydrogen or forms an alkylene chain together with $R_3$ and $R_{11}$ and $R_{12}$ are the same or different and selected from hydrogen, halogen or alkyl, alkyl groups, alkoxy groups and moities thereof, they may be branched or straight $C_1$–$C_9$-chains or comprise cyclic alkyl groups, such as cycloakylalkyl.

Examples of proton pump inhibitors according to formula I are

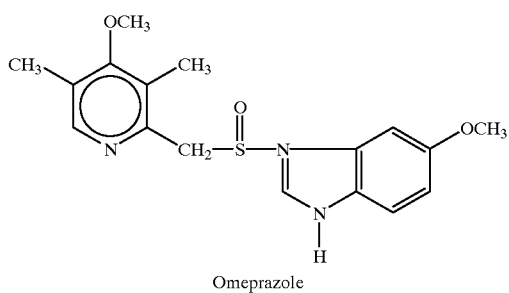

Omeprazole

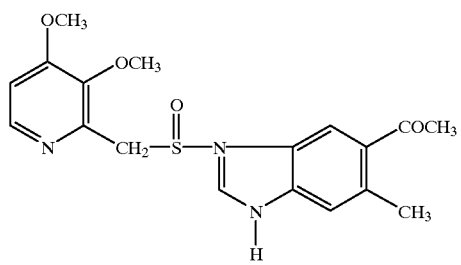

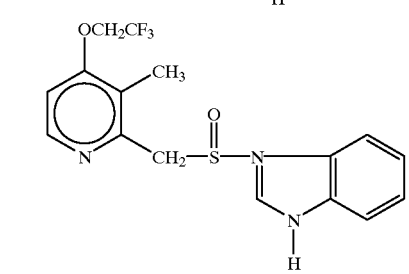

Lansoprazole

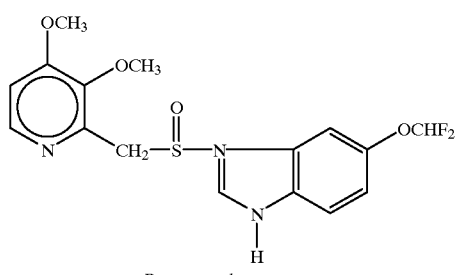

Pantoprazole

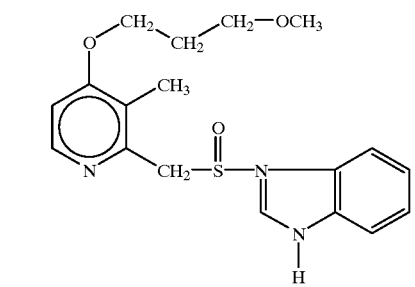

Pariprazole

Leminoprazole

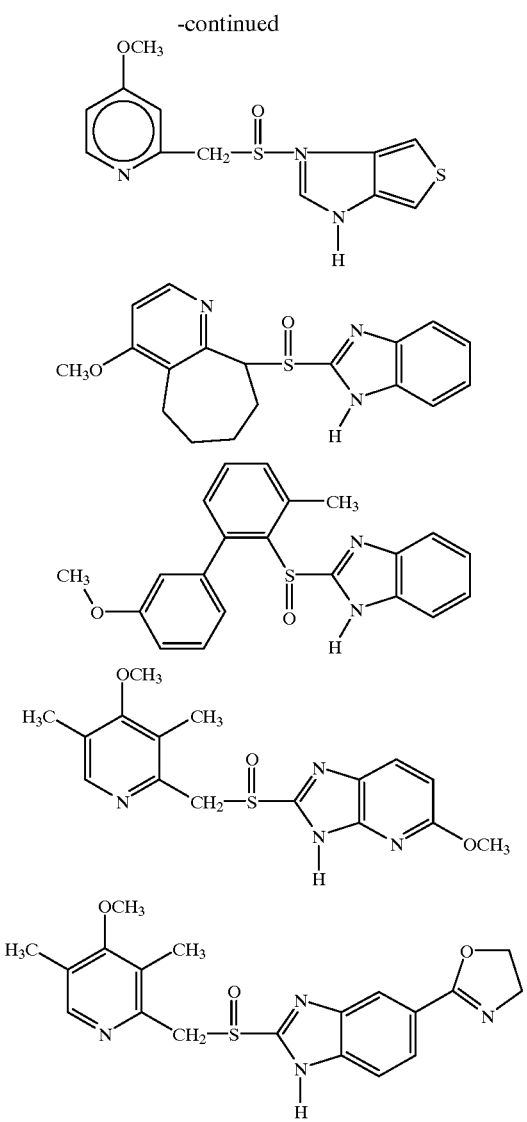

-continued

The proton pump inhibitors used in the dosage forms of the invention may be used in neutral form or in the form of an alkaline salt, such as for instance the $Mg^{2+}Ca^{2+}$, $Na^+$, $K^+$ or $Li^+$ salts, preferably the $Mg^{2+}$ salts. Further where applicable, the compounds listed above may be used in racemic form or in the form of a substantially pure enantiomer thereof, or alkaline salts of the single enantiomers.

Suitable proton pump inhibitors are for example disclosed in EP-A1-0005129, EP-A1- 174 726, EP-A1-166 287, GB 2 163 747 and WO90/06925, WO91/19711, WO91/19712, and further especially suitable compounds are described in WO95/01977 and WO94/27988.

The gastric acid suppressing agent is preferably an acid susceptible proton pump inhibitor but other gastric acid suppressing agents such as the $H_2$ receptor antagonists: ranitidine, cimetidine or famotidine, may be used together with a prokinetic agent in the pharmaceutical compositions according to the present invention.

A wide variety of prokinetic compounds may be used in combination with a suitable proton pump inhibitor in the fixed unit dosage form according to the present invention. Such prokinetic agents include for example cisapride, mosapride, metoclopramide, and domperidone. The active prokinetic agents could be in standard forms or used as salts, hydrates, esters etc. A combination of two or more of the above described drugs may be used. A preferable prokinetic agent for the new fixed dosage form is mosapride or cisapride. Such suitable prokinetic agents are described in EP 0 243 959 and EP 0 076 530.

The preferred multiple unit tableted dosage form comprising a proton pump inhibitor in the form of a racemate, an alkaline salt or one of its single enantiomers in combination with a prokinetic compound, is characterized in the following way. Individually enteric coating layered units (small beads, granules or pellets) containing the proton pump inhibitor and optionally alkaline reacting substances, are mixed with the prokinetic compound and conventionally tablet excipients. The prokinetic compound and tablet excipients may be dry mixed or wet-mixed into granules. The mixture of enteric coating layered units, prokinetic agent(s) and optionally excipients are compressed into the multiple unit tableted dosage forms. With the expression "individual units" is meant small beads, granules or pellets, in the following referred to as pellets of the proton pump inhibitor.

The compaction process (compression) for formulating the multiple unit tableted dosage form must not significantly affect the acid resistance of the enteric coating layered pellets. In other words the mechanical properties, such as the flexibility and hardness as well as the thickness of the enteric coating layer(s), must secure that the requirements on enteric coated articles in the United States Pharmacopeia are accomplished in that the acid resistance does not decrease more than 10% during the compression of the pellets into tablets.

The acid resistance is defined as the amount of proton pump inhibitor in the tablets or pellets after being exposed to simulated gastric fluid USP, or to 0.1 M HCl (aq) relative to that of unexposed tablets and pellets, respectively. The test is accomplished in the following way. Individual tablets or pellets are exposed to stimulated gastric fluid of a temperature of 37° C. The tablets disintegrate rapidly and release the enteric coating layered pellets to the medium. After two hours the enteric coating layered pellets are removed and analyzed for content of the proton pump inhibitor using High Performance Liquid Chromatography (HPLC).

Further specific components used in the fixed unit dosage forms of the present invention are defined below.

Core material—for Enteric Coating Layered Pellets Comprising a Proton Pump Inhibitor The core material for the individually enteric coating layered pellets can be constituted according to different principles. Seeds layered with the proton pump inhibitor, optionally mixed with alkaline substances, can be used as the core material for the further processing.

The seeds which are to be layered with the proton pump inhibitor can be water insoluble seeds comprising different oxides, celluloses, organic polymers and other materials, alone or in mixtures or water-soluble seeds comprising different inorganic salts, sugars, non-pareils and other materials, alone or in mixtures. Further, the seeds may comprise the proton pump inhibitor in the form of crystals, agglomerates, compacts etc. The size of the seeds is not essential for the present invention but may vary between approximately 0.1 and 2 mm. The seeds layered with the proton pump inhibitor are produced either by powder or solution/suspension layering using for instance granulation or spray coating layering equipment.

Before the seeds are layered, the proton pump inhibitor may be mixed with further components. Such components can be binders, surfactants fillers, disintegrating agents, alkaline additives or other and/or pharmaceutically acceptable ingredients alone or in mixtures. The binders are for example polymers such as hydroxypropyl methylcellulose (HPMC), hydroxypropylcellulose (HPC), carboxymethylcellulose sodium, polyvinyl pyrrolidone (PVP), or sugars, starches or other pharmaceutically acceptable substances with cohesive properties. Suitable surfactants are found in the groups of pharmaceutically acceptable non-ionic or ionic surfactants such as for instance sodium lauryl sulfate.

Alternatively, the proton pump inhibitor optionally mixed with alkaline substances and further mixed with suitable constituents can be formulated into a core material. Said core material may be produced by extrusion/spheronization, balling or compression utilizing conventional process equipment. The size of the formulated core material is approximately between 0.1 and 4 mm and preferably between 0.1 and 2 mm. The manufactured core material can further be layered with additional ingredients comprising the proton pump inhibitor and/or be used for further processing.

The proton pump inhibitor is mixed with pharmaceutical constituents to obtain preferred handling and processing properties and a suitable concentration of the substance in the final mixture. Pharmaceutical constituents such as fillers, binders, lubricants, disintegrating agents, surfactants and other pharmaceutically acceptable additives.

Further, the proton pump inhibitor may also be mixed with an alkaline, pharmaceutically acceptable substance (or substances). Such substances can be chosen among, but are not restricted to substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16}CO_3.4H_2O)$, $MgO.Al_2O_3.2SiO_2.nH_2O$ or similar comp pH-buffering substances such as trihydroxymethyl-aminomethane, basic amino acids and their salts or other similar, pharmaceutically acceptable pH-buffering substances.

Alternafively, the aforementioned core material can be prepared by using spray drying or spray congealing technique.

Enteric Coating Layer(s)

Before applying the enteric coating layer(s) onto the core material in the form of individual pellets or tablets, the pellets or tablets may optionally be covered with one or more separating layer(s) comprising pharmaceutical excipients optionally including alkaline compounds such as pH-buffering compounds. This/these separating layer(s), separate(s) the core material from the outer layers being enteric coating layer(s). The separating layer(s) protecting the core material of a proton pump inhibitor should be water soluble or rapidly disintegrating in water.

The separating layer(s) can be applied to the core material by coating or layering procedures in suitable equipments such as coating pan, coating granulator or in a fluidized bed apparatus using water and/or organic solvents for the coating process. As an alternative the separating layer(s) can be applied to the core material by using powder coating technique. The materials for the separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethyl-cellulose, hydroxypropyl methyl cellulose, carboxymethylcellulose sodium and others, used alone or in mixtures. Additives such as plasticizers, colorants, pigments, fillers anti-tacking and anti-static agents, such as for instance magnesium stearate, titanium dioxide, talc and other additives may also be included into the separating layer(s).

When the optional separating layer, is applied to the core material it may constitute a variable thickness. The maximum thickness of the separating layer(s) is normally only limited by processing conditions. The separating layer may serve as a diffusion barrier and may act as a pH-buffering zone. The pH-buffering properties of the separating layer(s) can be further strengthened by introducing into the layer(s) substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgO.CO_2.12H_2O$, $(Mg_6Al_2(OH)_{16}CO_3.4H_2O)$, $MgO.Al_2O_3.2SiO_2.nH_2O$, aluminium hydroxide/sodium bicarbonate coprecipitate or similar compounds; or other pharmaceutically acceptable pH-buffering compounds such as, for instance the sodium, potassium, calcium, magnesium and aluminium salts of phosphoric, carbonic, citric or other suitable, weak, inorganic or organic acids; or suitable organic bases, including basic amino acids and salts thereof Talc or other compounds may be added to increase the thickness of the layer(s) and thereby strenghten the diffusion barrier. The optionally applied separating layer(s) is not essential for the invention. However, the separating layer(s) may improve the chemical stability of the active substance and/or the physical properties of the novel multiple unit tableted dosage form.

Alternatively, the separating layer may be formed in situ by a reaction between an enteric coating polymer layer applied on the core material an alkaline reacting compound in the core material. Thus, the separating layer formed comprises a salt formed between the enteric coating layer polymer(s) and an alkaline reacting compound which is in the position to form a salt.

One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers one or more, separately or in combination, of the following can be used, e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s).

The enteric coating layers may contain pharmaceutically acceptable plasticizers to obtain the desired mechanical properties, such as flexibility and hardness of the enteric coating layers. Such plasticizers are for instance, but not restricted to triacetin, citric acid esters, phthalic acid esters, dibutyl sebacate, cetyl alcohol, polyethylene glycols, polysorbates or other plasticizers.

The amount of plasticizer is optimized for each enteric coating layer formula, in relation to selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that the acid resistance of the pellets covered with enteric coating layer(s) does not decrease significantly during compression of pellets into tablets. The amount of plasticizer is usually above 10% by weight of the enteric coating layer polymer(s), preferably 15–50% and more preferably 20–50%. Additives such as dispersants, colorants, pigments polymers e.g. poly (ethylacrylate, methylinethacrylate), anti-tacking and anti-foaming agents may also be included into the enteric coating layer(s). Other compounds may be added to increase film thickness and to decrease diffusion of acidic gastric juices into the acid susceptible material.

To protect the acid susceptible substance, the proton pump inhibitor, and to obtain an acceptable acid resistance of the dosage form according to the invention, the enteric coating layer(s) constitutes a thickness of approximately at least 10 $\mu$m, preferably more than 20 $\mu$m. The maximum thickness of the applied enteric coating is normally limited by processing conditions and the desired dissolution profile.

Alternatively the enteric coating layer described above may be used for enteric coating of conventional tablets comprising an acid susceptible proton pump inhibitor. Said enteric coating layered tablet is thereafter presscoated with a granulation comprising the prokinetic compound.

Over-coating Layer

Pellets covered with enteric coating layer(s) may further be covered with one or more over-coating layer(s). The over-coating layer(s) should be water soluble or rapidly disintegrating in water. The over-coating layer(s) can be applied to the enteric coating layered pellets by coating or layering procedures in suitable equipments such as coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and others, used alone or in mixtures. Additives such as plasticizers, colorants, pigments, fillers, anti-tacking and anti-static agents, such for instance magnesium stearate, titaniumdioxide, talc and other additives may also be included into the over-coating layer(s). Said over-coating layer may further prevent potential agglomeration of enteric coating layered pellets, further protect the enteric coating layer towards cracking during the compaction process and enhance the tableting process. The maximum thickness of the applied over-coating layer(s) is normally limited by processing conditions and the desired dissolution profile.

The above described over-coating layer may also be used as a tablet filmcoat to obtain tablets of good appearance.

Prokinetic Preparation

The active substance(s) in form of one or more prokinetic compound(s) is dry mixed with inactive excipients and the mixture is wet massed with a granulation liquid. The wet mass is dried preferably to a loss on drying of less than 3% by weight. Thereafter the dry mass is milled to a suitable size for the granules, such as smaller than 4 mm, and preferably smaller than 1 mm. Suitable inactive excipients for the prokinetic mixture are for instance lactose, corn starch low substituted hydroxypropyl cellulose, microcrystalline cellulose, sodium starch glycolate and crosslinked polyvinyl pyrrolidone. The dry mixture comprising prokinetic compound is wet-mixed with a suitable granulation liquid comprising for instance hydroxy propyl cellulose or polyvinyl pyrrolidone dissolved in purified water or an alcohol or a mixture thereof. Alternatively, the prokinetic agent(s) are dry mixed with pharmaceutically acceptable excipients according to above.

As a further alternative, the prokinetic agent(s) can be applied in a separate layer onto a multiple unit tableted dosage form or surrounding the tablet comprising the proton pump inhibitor. The prokinetic agent(s) is dispersed or dissolved in an aqueous solution optionally comprising binders for suspension layering onto the tablet.

Multiple Unit Tablets

The enteric coating layered pellets comprising a proton pump inhibitor are mixed with the granules comprising prokinetic compound and tablet excipients such as fillers, binders, disintegrants, lubricants and other pharmaceutically acceptable additives. The mixture is compressed into a multiple unit tableted dosage form. The compressed tablet is optionally covered with a filmforming agent(s) to obtain a smooth surface of the tablet and further enhance the stability of the tablet during packaging and transport. Such a coating layer may further comprise additives such as anti-tacking agents, colorants and pigments or other additives to obtain a tablet of good appearance.

Alternatively the enteric coated pellets may be dry mixed with the prokinetic compound and pharmaceutically acceptable tablet excipients according to above, and compressed into tablets (direct compression).

Suitable lubricants for the tableting process are for instance sodium stearyl fumarate, magnesium stearate and talc.

Further, the different active substances may be formulated into different layers, wherein the layer comprising the proton pump inhibitor is in the form of a multiple unit tableted dosage form layered with prepared prokinetic granules. The two layers may be separated by an anti-tacking layer.

As a further alternative the proton pump inhibitor is dry mixed with inactive excipients and compressed into a conventional tablet which is coating layered with an enteric coating and optionally a separating layer is applied before the enteric coating. Thereafter the enteric coated tablet is presscoated with a prokinetic preparation. The tablet core may also be formulated as a multiple unit tableted dosage form comprising the proton pump inhibitor, the tablet is spray coating layered by a suspension comprising the prokinetic agent(s).

The fraction of enteric coating layered pellets constitutes less than 75% by weight of the total tablet weight and preferably less than 60%. By increasing the amount of the granules comprising the prolinetic agent the fraction of enteric coating layered pellets of the proton pump inhibitor may be reduced in the multiple unit tableted dosage form. By choosing small enteric coating layered pellets in the formulation according to the present invention, the number of pellets in each tablet can be held high which in turn makes the tablet divisible with retained dosing accuracy.

Thus, the preferred multiple unit tablet formulation consists of enteric coating layered pellets containing one active substance in the form of a proton pump inhibitor, optionally admixed with alkaline reacting compound(s), compressed into tablets together with the prepared prokinetic mixture and optionally tablet excipients. The addition of an alkaline reacting material to the proton pump inhibitor is not necessary, in any sense but such a substance may further enhance the stability of the proton pump inhibitor or some of the alkaline reacting compounds may react in situ with the enteric coating material to form a separating layer. The enteric coating layer(s) is making the pellets of the dosage form insoluble in acidic media, but disintegrating/dissolving in near neutral to alkaline media such as, for instance the liquids present in the proximal part of the small intestine, where dissolution of the proton pump inhibitor is desired. The prokinetic agent(s) may be released in the stomach. The enteric coating layered pellets may further be covered with an overcoating layer before being formulated into the tablet and they may also contain one or more separating layer(s) optionally containing alkaline substance(s).

Process

The process for the manufacture of the dosage form represents a further aspect of the invention. After formulation of the pellets by spray coating or layering of the proton pump inhibitor onto seeds, or by extrusion/spheronization or granulation, e.g. rotor granulation of homogeneous pellets, the pellets are first optionally covered with the separating layer(s) and then with the enteric coating layer(s) or a separating layer is spontaneously developed in situ between the alkaline core material and the enteric coating layer material. The coating is carried out as described above and in the accompanying examples. The preparation of the prokinetic mixture is also described above and in the examples. The pharmaceutical processes can preferably be completely water-based.

The enteric coating layered pellets, with or without an over-coat, are mixed with the prepared prokinetic mixture, optionally tablet excipients and other pharmaceutically acceptable additives and compressed into tablets. Alternatively, the enteric coating layered pellets may be intimately mixed with tablet excipients and precompressed and further layered with the prepared prokinetic mixture and finally compressed into a tablet. As a further alternative the proton pump inhibitor in form of the active substance may be mixed with tablet excipients and compressed into a tablet which is optionally layered with a separating layer and thereafter enteric coating layered. Said tablet is then press-coated with the prepared prokinetic mixture. Alternatively, a multiple unit tableted dosage form of the proton pump inhibitor is manufactured as describes above. The multiple unit dosage form is spray coating layered by an aqueous suspension comprising the prokinetic agent(s). The suspension may optionally comprise binders; such as hydroxypropyl methylcellulose, and an alcohol to solve the binder. The proton pump inhibitor in the form of enteric coating layered pellets may also be filled into a capsule together with the prokinetic substance in the form of a granulation optionally mixed with pharmaceutical excipients.

Use of the Preparation

The dosage forms according to the invention are especially advantageous in the treatment of gastro oesophageal reflux disease and other gastrointestinal disorder. They are administered one to several times a day, preferably once or twice daily. The typical daily dose of the active substances varies and will depend on various factors such as the individual requirements of the patients, the mode of administration and disease. In general each dosage form will comprise 0.1–200 mg of the proton pump inhibitor and 0.1–100 mg of the prokinetic compound. Preferably, each dosage form will comprise 10–80 mg of the proton pump inhibitor and 3–80 mg of the prokinetic compound, and more preferably 10–40 mg of proton pump inhibitor and 15–40 mg of the prokinetic compound, respectively.

The multiple unit tablet preparation is also suitable for dispersion in an aqueous liquid with slightly acidic pH-value before being orally administered or fed through a nasogastric tube.

The invention is illustrated more in detail in the following examples.

EXAMPLES

Example 1

Multiple unit dosage form comprising magnesium omeprazole and mosapride (batch size 500 tablets).

| Core material | |
|---|---|
| Magnesium omeprazole | 5 kg |
| Sugar sphere seeds | 10 kg |
| Hydroxypropyl methylcellulose | 0.75 kg |
| Water purified | 20.7 kg |
| Separating layer | |
| Core material (acc. to above) | 10.2 kg |
| Hydroxypropyl cellulose | 1.02 kg |
| Talc | 1.75 kg |
| Magnesium stearate | 0.146 kg |
| Water purified | 21.4 kg |
| Enteric coating layer | |
| Pellets covered with separating layer (acc. to above) | 11.9 kg |
| Methacrylic acid copolymer (30% suspension) | 19.8 kg |
| Triethyl citrate | 1.79 kg |
| Mono- and diglycerides (NF) | 0.297 kg |
| Polysorbate 80 | 0.03 kg |
| Water purified | 11.64 kg |
| Over-coating layer | |
| Enteric coating layered pellets (acc. to above) | 20 kg |
| Hydroxypropyl methylcellulose | 0.238 kg |
| Magnesium stearate | 0.007 kg |
| Water purified | 6.56 kg |
| Tablets | |
| Prepared pellets comprising omeprazole (acc. to above) | 41.2 g |
| Mosapride citrate dihydrate | 23.4 g |
| Microcrystalline cellulose | 138.1 g |
| Polyvinyl pyrrolidone crosslinked | 2.9 g |
| Sodium stearyl fumarate | 0.29 g |
| Tablet coating solution (for 10 kg tablets) | |
| Hydroxypropyl methylcellulose | 250 g |
| Polyethylene glycol 6000 | 62.5 g |
| Titanium dioxide | 62.5 g |
| Water purified | 2125 g |
| Hydrogen pyroxide | 0.75 g |

Suspension layering was performed in a fluid bed apparatus. Magnesium omeprazole was sprayed onto sugar sphere seeds from a water suspension containing the dissolved binder. The size of sugar sphere seeds were in the range of 0.25 to 0.35 mm.

The prepared core material was covered with a separating layer in a fluid bed apparatus with a hydroxypropyl cellulose solution containing talc and magnesium stearate. The enteric coating layer consisting of methacrylic acid copolymer, mono- and diglycerides, triethyl citrate and polysorbate was sprayed onto the pellets covered with a separating layer in a fluid bed apparatus. In a fluid bed apparatus enteric coating layered pellets were coated with a hydroxypropyl methylcellulose solution containing magnesium stearate. The over-coating layered pellets were classified by sieving.

The enteric coating layered pellets with an over-coating layer, mosapride citrate dihydrate, microcrystalline cellulose, polyvinyl pyrrolidone crosslinked and sodium stearyl fumarate were dry mixed and compressed into tablets using an excenter tableting machine equipped with 12 mm punches. The amount of omeprazole in each tablet was approx. 10 mg and the amount of mosapride was approx. 30 mg. The tablet hardness was measured to 70–80 N.

The obtained tablets are covered with a conventional tablet filmcoating layer.

Example 2

Multiple unit dosage form comprising magnesium omeprazole and mosapride (batch size 500 tablets).

| Mosapride granulation | |
|---|---|
| Mosapride citrate dihydrate | 46.8 g |
| Lactose monohydrate | 350 g |
| Corn starch | 184 g |
| Hydroxy propyl cellulose LF | 25 g |
| Water purified | 225 g |
| Hydroxypropyl cellulose (L-HPC) | 152 g |
| Magnesium stearate | 7.4 g |
| Tablets | |
| Enteric coating layered pellets with an over-coating layer (manufacturing and composition as in example 1) | 41.2 g |
| Mosapride granulation | 190 g |
| Tablet coating solution (for 10 kg tablets) | |
| Hydroxypropyl methyl cellulose | 250 g |
| Polyethylene glycol 6000 | 62.5 g |
| Titaniumdioxid | 62.5 g |
| Water purified | 2125 g |
| Hydrogen peroxide | 0.75 g |

Hydroxypropyl cellulose was dissolved in purified water to form the granulation liquid. Mosapride citrate dihydrate, lactose monohydrate and corn starch were dry mixed. The granulation liquid was added to the powder mixture and the mass was wet-mixed. The wet mass was dried in a steam-oven and milled through sive 1 mm in an oscillating mill equipment The prepared granulation was mixed with low substituted hydroxypropyl cellulose and magnesium stearate.

The enteric coating layered pellets with an over-coat and prepared granules were mixed and compressed into tablets using an excenter tableting machine equipped with 11 mm punches. The amount of omeprazole in each tablet was approx. 10 mg and the amount of mosapride was approx. 15 mg. Tablet hardness was measured to 30–40 N.

The obtained tablets are covered with a conventional tablet filmcoating layer.

Example 3

Multiple unit dosage form comprising magnesium omeprazole and mosapride (batch size 500 tablets).

| Core material | |
|---|---|
| Magnesium omeprazole | 10 kg |
| Sugar sphere seeds | 10 kg |
| Hydroxypropyl methylcellulose | 1.5 kg |
| Water purified | 29.9 kg |
| Separating layer | |
| Core material (acc. to above) | 20 kg |
| Hydroxypropyl cellulose | 2 kg |
| Talc | 3.43 kg |
| Magnesium stearate | 0.287 kg |
| Water purified | 41 kg |
| Enteric coating layer | |
| Pellets covered with separating layer (acc. to above) | 24.5 kg |
| Methacrylic acid copolymer (30% suspension) | 32.7 kg |
| Triethyl citrate | 2.94 kg |
| Mono-and diglycerides (NF) | 0.49 kg |
| Polysorbate 80 | 0.049 kg |
| Water purified | 19.19 kg |
| Over-coating layer | |
| Enteric coating layered pellets (acc. to above) | 37.8 kg |
| Hydroxypropyl methylcellulose | 0.49 kg |
| Magnesium stearate | 0.0245 kg |

-continued

| | |
|---|---|
| Water purified | 11.6 kg |
| Tablets | |
| Prepared pellets comprising omeprazole (acc. to above) | 47.45 g |
| Mosapride citrate dihydrate | 23.4 g |
| Microcrystalline cellulose | 163 g |
| Polyvinyl pyrrolidone crosslinked | 3.3 g |
| Sodium stearyl fumarate | 0.3 g |
| Tablet coating solution (for 10 kg tablets) | |
| Hydroxypropyl methyl cellulse | 250 g |
| Polyethylene glycol 6000 | 62.5 g |
| Titanium dioxid | 62.5 g |
| Water purified | 2125 g |
| Hydrogen peroxide | 0.75 g |

The enteric coating layered pellets with an over-coating layer prepared as described in Example 1, mosapride citrate dihydrate, microcrystalline cellulose, polyvinyl pyrrolidone crosslinked and sodium stearyl fumarate were dry mixed and compressed into tablets using an excenter tableting machine equipped with 12 mm punches. The amount of omeprazole in each tablet was approx. 20 mg and the amount of mosapride was approx. 30 mg. The tablet hardness was measured to 70 N.

The tablets are covered with a conventional tablet film-coating layer.

Example 4

Multiple unit dosage form comprising S-omeprazole magnesium salt and mosapride (batch size 300 tablets).

| Core material | |
|---|---|
| S-omeprazole magnesium salt | 120 g |
| Sugar sphere seeds | 150 g |
| Hydroxypropyl methylcellulose | 18 g |
| Polysorbate 80 | 2.4 g |
| Water purified | 562 g |
| Separating layer | |
| Core material (acc. to above) | 200 g |
| Hydroxypropyl cellulose | 30 g |
| Talc | 51.4 g |
| Magnesium stearate | 4.3 g |
| Water purified | 600 g |
| Enteric coating layer | |
| Pellets covered with separating layer (acc. to above) | 250 g |
| Methacrylic acid copolymer (30% suspension) | 333.7 g |
| Triethyl citrate | 30 g |
| Mono- and diglycerides (NF) | 5 g |
| Polysorbate 80 | 0.5 g |
| Water purified | 196 g |
| Tablets | |
| Prepared pellets comprising (s)-omeprazole Mg-salt (acc. to above) | 38.2 g |
| Mosapride citrate dihydrate | 14 g |
| Microcrystalline cellulose | 98.3 g |
| Polyvinyl pyrrolidone crosslirinked | 2.1 g |
| Sodium stearyl fumarate | 0.2 g |
| Tablet coating solution (for 10 kg tablet) | |
| Hydroxypropyl methyl cellulose | 250 g |
| Polyethylene glycol 6000 | 62.5 g |

| -continued | |
|---|---|
| Titaniumdioxid | 62.5 g |
| Water purified | 2125 g |
| Hydrogen peroxide | 0.75 g |

Suspension layering was performed in a fluid bed apparatus. S-Omeprazole magnesium salt was sprayed onto sugar sphere seeds from a water suspension containing the dissolved binder and polysorbate 80. The size of sugar sphere seedes were in the range of 0.25 to 0.35 mm.

The prepared core material was covered with a separating layer in a fluid bed apparatus with hydroxypropyl cellulose solution containing talc and magnesium stearate. The enteric coating layer consisting of methacrylic acid copolymer, mono-and diglycerides, triethyl citrate and polysorbate was sprayed onto the pellets covered with a separating layer in a fluid bed apparatus. The enteric coating layered pellets were classified by sieving.

The enteric coating layered pellets, mosapride citrate dihydrate, microcrystalline cellulose, polyvinyl pyrrolidone crosslinked and sodium stearyl fumarate were mixed and compressed into tablets using an excenter tableting machine equipped with 12 mm punches. The amount of S-omeprazole in each tablet was approx. 20 mg and the amount of mosapride was approx. 30 mg. The tablet hardness was measured to 65 N.

The tablets are covered with a conventional tablet film-coating layer.

| | "Acid resistance" i.e. % left after exposure to 0.1 N HCl for 2 hrs |
|---|---|
| | Tablets |
| Ex 1 | 97% |
| Ex 2 | 90% |
| Ex 3 | 102% |
| Ex 4 | 104% |

Example 5

Multiple unit dosage form comprising lanzoprazole and mosapride (batch size 500 tablets).

| Core material | |
|---|---|
| Lanzoprazole | 400 g |
| Sugar sphere seeds | 400 g |
| Hydroxypropyl methylcellulose | 80 g |
| Sodium laurylsulfate | 3 g |
| Water purified | 1500 g |
| Separating layer | |
| Core material (acc. to above) | 400 g |
| Hydroxypropyl cellulose | 40 g |
| Talc | 69 g |
| Magnesium stearate | 6 g |
| Water purified | 800 g |
| Enteric coating layer | |
| Pellets covered with a separating layer (acc. to above) | 400 g |
| Methacrylic acid copolymer (30% suspension) | 667 g |
| Triethyl citrate | 60 g |
| Mono- and diglycerides (NF) | 10 g |

| -continued | |
|---|---|
| Polysorbate 80 | 1 g |
| Water purified | 420 g |
| Tablets | |
| Prepared pellets comprising lanzoprazple (acc. to above) | 47 g |
| Mosapride citrate dihydrate | 46.8 g |
| Microcrystalline cellulose | 261 g |
| Polyvinyl pyrrolidone crosslinked | 5 g |
| Sodium stearyl fumarate | 0.5 g |
| Tablet coating solution (for 10 kg tablets) | |
| Hydroxypropyl methylcellulose | 250 g |
| Polyethylene glycol 6000 | 62.5 g |
| Titanium dioxid | 62.5 g |
| Water purified | 2125 g |
| Hydrogen peroxide | 0.75 g |

Suspension layering was performed in a fluid bed apparatus. Lansoprazole was sprayed onto the sugar sphere seeds from a suspension containing the dissolved binder in a water solution. Pellets covered with separating layer and enteric coating layer were produced as in example 1.

The enteric coating layered pellets, mosapride citrate dihydrate, microcrystalline cellulose, polyvinyl pyrrolidone crosslinked and sodium stearyl fumarate were dry mixed and compressed into tablets using an excenter tableting machine equipped with 10 mm punches. The amount of lanzoprazole in each tablet was approx. 10 mg and the amount of mosapride was approx. 30 mg. The tablet hardness was measured to 70 N.

The tablets are covered with a conventional tablet film-coating layer.

Example 6

Magnesium omeprazole and mosapride presscoated tablets (batch size 10.000 tablets).

| Omeprazole tablets | |
|---|---|
| Mg-omeprazole | 112.5 g |
| Mannitol | 287 g |
| Microcrystalline cellulose | 94 g |
| Sodium starch glycolate | 30 g |
| Hydroxypropyl methylcellulose | 30 g |
| Talc | 25 g |
| Microcrystalline cellulose | 31 g |
| Sodium stearyl fumarate | 12.5 g |
| Water purified | 200 g |
| Solution for separating layer (for 10 kg tablets) | |
| Hydroxypropyl methylcellulose | 300 g |
| Hydrogen peroxide (30%) | 0.003 g |
| Water purified | 2700 g |
| Solution for enteric coating layer (for 10 kg tablets) | |
| Methacrylic acid copolymer dispersion (30%) | 2450 g |
| Polyethylene glycol 400 | 80 g |
| Titanium dioxide Colour | 100 g |
| Water purified | 1960 g |
| Presscoated tablet | |
| Mg-Omeprazole tablets | 10.000 tabl |
| Mosapride granulation | 3800 g |
| (manufacturing and composition as in example 2) | |
| Tablet coating solution (for 10 kg tablets) | |
| Hydroxypropyl methylcellulose | 250 g |
| Polyethylene glycol 6000 | 62.5 g |
| Titaniumdioxid | 62.5 g |

| -continued | |
|---|---|
| Water purified | 2125 g |
| Hydrogen peroxide | 0.75 g |

Magnesium omeprazole, mannitol, microcrystalline cellulose, sodium starch glycolate and hydroxypropyl methyl cellulose are dry mixed. The powder mixture is moistened with water purified. The granulation is dried and milled through sive 1 mm in a suitable mill. The prepared granules comprising proton pump inhibitor is mixed with talc, microcrystalline cellulose and sodium stearyl fumarate and compressed into tablets using a rotary tableting machine equipped with 5 mm punches.

The obtained tablets are coated layered with a separating layer and an enteric coating layer. Said tablets are then presscoated with mosapride granulation using a presscoating machine equipped with 11 mm punched.

The tablets are covered with a conventional tablet filmcoating layer.

Example 7

A capsule formulation comprising magnesium omeprazole and mosapride (batch size 100 capsules).

| Capsules | |
|---|---|
| Enteric coating layered pellets with an over-coating layer (manufacturing and composition as in example 3) | 9.49 g |
| Mosapride granulation (manufacturing and composition as in example 2) | 38 g |

Enteric coating layered pellets and mosapride granulation are filled into capsules, size 00. The amount of omeprazole in each capsule is approx. 20 mg and the amount of mosapride is approx. 15 mg.

Example 8

Multiple unit dosage form comprising magnesium omeprazole with a tablet coating layer comprising mosapride (batch size 1000 tablets).

| Tablets | |
|---|---|
| Enteric coating layered pellets with an overcoat (manufacturing and composition as in example 1) | 82.4 g |
| Microcrystalline cellulose | 179.2 g |
| Polyvinyl pyrrolidone crosslinked | 3.7 g |
| Sodium stearyl fumarate | 0.4 g |
| Mosapride coating layer suspension | |
| Mosapride citrate dihydrate | 23.4 g |
| Hydroxypropyl methyl cellulose | 13.4 g |
| Ethanol 99% | 132.5 g |
| Water purified | 132.5 g |
| Tablet coating solution (for 10 kg tablets) | |
| Hydroxypropyl methylcellulose | 250 g |
| Polyethylene glycol 6000 | 62.5 g |
| Titanium dioxid | 62.5 g |
| Water purified | 2125 g |
| Hydrogen peroxide | 0.75 g |

The enteric coating layered pellets are mixed with microcrystalline cellulose, polyvidone and sodium stearyl fumarate and compressed into tablets using an excenter tableting machine equipped with 9 mm punches. The tablets are then coated layered in a fluid bed apparatus with the suspension comprising mosapride. The amount of omeprazole in each tablet is approx. 10 mg and the amount of mosapride is approx. 15 mg.

Finally the tablets are covered with a conventional tablet filmcoating layer.

The best mode to practise the invention is according to compositions described in Examples 1 and 4.

The enteric coating layered pellets comprising a proton pump inhibitor may also be prepared as described in the following examples.

Example 9

Preparation of enteric coating layered pellets by extrusion/spheronization.

| Core material | |
|---|---|
| Magnesium omeprazole | 600 g |
| Mannitol | 1000 g |
| Microcrystalline cellulose | 300 g |
| Hydroxypropyl cellulose | 100 g |
| Sodium lauryl sulphate | 6 g |
| Water purified | 802 g |
| Separating layer | |
| Core material | 400 g |
| Hydroxypropyl methylcellulose | 48 g |
| Water purified | 960 g |
| Enteric coating layer | |
| Pellets covered with separating layer | 200 g |
| Methacrylic acid copolymer | 100 g |
| Triethyl citrate | 30 g |
| Mono- and diglycerides (NF) | 5 g |
| Polysorbate 80 | 0.5 g |
| Water purified | 309 g |

Sodium lauryl sulphate is dissolved in purified water to form the granulation liquid. Magnesium omeprazole, mannitol, microcrystalline cellulose and hydroxypropyl cellulose are dry-mixed. The granulation liquid is added to the powder mixture and the mass is wet-mixed.

The wet mass is forced through an extruder equipped with screens of size 0.5 mm. The extrudate is spheronized on a friction plate in a spheronizing apparatus. The core material is dried in a fluid bed dryer and classified. The prepared core material is covered by a separating layer in a fluid bed apparatus with a hydroxypropyl methylcellulose/water solution.

The enteric coating layer is applied to the pellets covered with separating layer from an aqueous dispersion of methacrylic acid copolymer plasticized with triethyl citrate to which a mono- and diglycerides/polysorbate dispersion has been added. The pellets are dried in a fluid bed apparatus.

Example 10

Preparation of enteric coating layered pellets by powder.

| Core material | |
| --- | --- |
| Magnesium omeprazole | 1500 g |
| Sugar sphere seeds | 1500 g |
| Hydroxypropyl methylcellulose | 420 g |
| Aerosil ® | 8 g |
| Water purified | 4230 g |
| Separating layer | |
| Core material | 500 g |
| Hydroxypropyl cellulose | 40 g |
| Talc | 67 g |
| Magnesium stearate | 6 g |
| Water purified | 800 g |
| Enteric coating layer | |
| Pellets covered with separating layer | 500 g |
| Methacrylic acid copolymer | 200 g |

Magnesium omeprazole, part of the hydroxypropyl methylcellulose and Aerosil® are dry-mixed forming a powder. Sugar sphere seeds (0.25–0.40 mm) are layered with the powder in a centrifugal fluidized coating granulator while spraying a hydroxypropyl methylcellulose solution (6%, w/w).

The prepared core material is dried and covered by a separating layer in a centrifugal fluidized coating-granulator. A fluid bed apparatus is used for enteric coating layereing.

Example 11

Preparation of enteric coating layered pellets with of silicon dioxide seeds.

| Core material | |
| --- | --- |
| Magnesium omeprazole | 8.00 kg |
| Silicon dioxide | 8.00 kg |
| Hydroxypropyl methylcellulose | 1.41 kg |
| Sodium lauryl sulphate | 0.08 kg |
| Water purified | 28.00 kg |
| Separating layer | |
| Core material | 10.00 kg |
| Hydroxypropyl methylcellulose | 0.80 kg |
| Water purified | 10.00 kg |
| Enteric coating layer | |
| Pellets covered with separating layer | 300 g |
| Methacrylic acid copolymer | 124 g |
| Polyethylene glycol 400 | 25 g |
| Mono- and diglycerides (NF) | 3 g |
| Polysorbate 80 | 1 g |
| Water purified | 463 g |

Suspension layering is performed in a fluid bed apparatus. Magnesium omeprazole is sprayed onto the silicon dioxide seeds from a water suspension containing the dissolved binder and a surface active ingredient.

The prepared core material is covered with a separating layer in a fluid bed apparatus with a hydroxypropyl methylcellulose solution. The enteric coating layer consisting of methacrylic acid copolymer, mono- and diglycerides, polyethylene glycol 400 and polysorbate is sprayed onto the pellets covered with separating layer in a fluid bed apparatus.

Example 12

Preparation of enteric coating layered pellets.

| Enteric coating layer | |
| --- | --- |
| Pellets covered with separating layer | 500 g |
| (manufacturing and composition as in example 10) | |
| Methacrylic acid copolymer | 250 g |
| Polyethylene glycol 6000 | 75 g |
| Mono- and diglycerides (NF) | 12.5 g |
| Polysorbate 80 | 1.2 g |
| Water purified | 490 g |

Example 13

Preparation of enteric coating layered pellets.

| Enteric coating | |
| --- | --- |
| Pellets covered with separating layer | 500 g |
| (manufacturing and composition as in example 1) | 250 g |
| Hydroxypropyl methylcellulose phthalate | |
| Cetanol | 50 g |
| Ethanol (95%) | 1000 g |
| Acetone | 2500 g |

Example 14

Preparation of enteric coating layered pellets.

| Core material | |
| --- | --- |
| Omeprazole | 225 g |
| Mannitol | 1425 g |
| Hydroxypropyl cellulose | 60 g |
| Microcrystalline cellulose | 40 g |
| Lactose anhydrous | 80 g |
| Sodium lauryl sulphate | 5 g |
| Disodium hydrogen phosphate dihydrate | 8 g |
| Water purified | 350 g |
| Separating layer | |
| Core material | 300 g |
| Hydroxypropyl cellulose | 30 g |
| Talc | 51 g |
| Magnesium stearate | 4 g |
| Enteric coating layer | |
| Pellets covered with separating layer | 300 g |
| Methacrylic acid copolymer | 140 g |
| Triethyl citrate | 42 g |
| Mono- and diglycerides (NF) | 7 g |
| Polysorbate 80 | 0.7 g |

The dry ingredients for producing the core material are well mixed in a mixer. Addition of granulation liquid is made and the mixture is kneaded and granulated to a proper consistency. The wet mass is pressed through an extruder screen and the granules are converted into a spherical form in a spheronizer. The core material is dried in a fluid bed apparatus and classified into a suitable particle size range, e.g. 0.5–1.0 mm The prepared core material is covered with a separating layer and enteric coating layered as described in previous examples.

Preparation of Active Substance

Magnesium omeprazole used in some of the examples is produced according to the process described in WO95/

01977, the single enantiomers of omeprazole salts are prepared as described in WO94/27988 and omeprazole is produced according to the process disclosed in EP-Al 0005129. These documents are hereby incorporated in a whole by reference.

What is claimed is:

1. An oral pharmaceutical composition comprising, as a first component, an acid susceptible proton pump inhibitor, and as a separate second component, at least one prokinetic agent, and as an optional third component, pharmaceutically acceptable excipients, wherein: (a) the composition is in the form of a multiple unit tablet; (b) the first component is in the form of pellets covered with an enteric coating layer; (c) the second component is separated from the first component by the enteric coating layer covering the first component; and (d) the enteric coating layer has mechanical properties such that the acid resistance of the enteric coated pellets is not significantly affected by compression of the pellets with the other tablet components during tableting.

2. The composition according to claim 1, wherein the proton pump inhibitor is covered by a separating layer located underneath the enteric coating layer.

3. The composition according to claim 1, wherein the tableted dosage form comprises a proton pump inhibitor and one prokinetic agent.

4. The composition according to claim 1, wherein the proton pump inhibitor is omeprazole, an alkaline salt of omeprazole, a single enantiomer of omeprazole or an alkaline salt of the single enantiomer.

5. The composition according to claim 4, wherein the proton pump inhibitor is S-omeprazole magnesium salt.

6. The composition according to claim 1, wherein the proton pump inhibitor is lansoprazole, an alkaline salt of lansoprazole, a single enantiomer of lansoprazole or an alkaline salt of the single enantiomer.

7. The composition according to any one of claims 4–6, wherein the prokinetic agent is mosapride.

8. The composition according to any one of claims 4–6, wherein the prokinetic agent is cisapride.

9. The composition according to claim 1, wherein the amount of the proton pump inhibitor is in the range of 10–80 mg, and the amount of the second component is in the range of 3–80 mg.

10. The composition according to claim 1, wherein the amount of the proton pump inhibitor is in the range of 10–40 mg, and the amount of the second component is in the range of 15–40 mg.

11. The composition according to claim 1, wherein the tableted dosage form comprises a first layer comprising the proton pump inhibitor and a separate second layer comprising the second component.

12. The composition according to claim 1, wherein the acid resistance of the enteric coating layered pellets is in compliance with the requirements on enteric coating layered articles defined in the United States Pharmacopeia.

13. The composition according to claim 1, wherein the acid resistance of the enteric coating layered pellets does not decrease more than 10% upon the tableting of the pellets into the multiple unit dosage form.

14. The composition according to claim 1, wherein the enteric coating pellets comprises a plasticized enteric coating layer material.

15. The composition according to claim 1, wherein the enteric coating layered pellets are further covered with an over-coating layer comprising pharmaceutically acceptable excipients.

16. The composition according to claim 1, wherein the tablet is divisible.

17. The composition according to claim 16, wherein the tablet is dispersible to form a slightly acidic aqueous suspension comprising the second component and the enteric coating pellets comprising a proton pump inhibitor.

18. The composition according to claim 1, wherein the proton pump inhibitor is in the form of a multiple unit dosage form layered with a coating layer comprising the second component.

19. A process for the manufacture of a composition in the form of a multiple unit tableted dosage form comprising, as a first component, a proton pump inhibitor, and as a separate second component, at least one prokinetic agent, comprising the steps of (a) preparing the proton pump inhibitor in the form of enteric coating layered pellets;

(b) mixing the enteric coated pellets with the second component and an optional pharmaceutically acceptable tablet excipient; and (c) compressing the mixture to form a multiple unit tablet without affecting any significant change of the acid resistance of the enteric coating layered pellets.

20. A process for the manufacture of a composition in the form of a multiple unit tableted dosage form having separate layers and comprising, as a first component in one layer a proton pump inhibitor, and as a second component in a separate second layer, at least one prokinetic agent, comprising the steps of:

(a) preparing the proton pump inhibitor in the form of enteric coating layered pellets;

(b) mixing the enteric coated pellets with pharmaceutically acceptable tablet excipients;

(c) drying the mixture;

(d) compressing the dry mixture into a multiple unit tablet without affecting any significant change of the acid resistance of the enteric coating layered pellets; and (e) spraying a coating layer comprising an aqueous suspension of the second component onto the multiple unit tableted dosage form; or (f) applying a separate layer comprising the second component in admixture with pharmaceutically acceptable excipients onto the multiple unit tablet dosage form.

21. A method of treating disorders associated with gastro oesophageal reflux diseases in mammals and man comprising administering to a host in need thereof a therapeutically effective dose of a multiple unit dosage form according to any one of claims 1, 2–6, 9–11, 12–17 or 18.

22. The method according to claim 21, wherein the disorder is a gastric disorder associated with gastro oesophageal reflux diseases.

* * * * *

UNITED STATES PATENT AND TRADEMARK OFFICE
CERTIFICATE OF CORRECTION

PATENT NO. : 6,132,771
DATED : October 17, 2000
INVENTOR(S) : Depui et al.

It is certified that error appears in the above-identified patent and that said Letters Patent is hereby corrected as shown below:

In claim 14, col. 23, line 61, after "enteric coating" insert therefor - - of the - -.

Signed and Sealed this

Eighth Day of May, 2001

Attest:

NICHOLAS P. GODICI

*Attesting Officer*     *Acting Director of the United States Patent and Trademark Office*